(12) United States Patent
Grotz

(10) Patent No.: US 9,808,345 B2
(45) Date of Patent: *Nov. 7, 2017

(54) RESILIENT ARTHROPLASTY DEVICE

(75) Inventor: R. Thomas Grotz, Novato, CA (US)

(73) Assignee: IORTHOPEDICS, INC., Las Vegas, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 12/460,703

(22) Filed: Jul. 23, 2009

(65) Prior Publication Data

US 2010/0023126 A1    Jan. 28, 2010

Related U.S. Application Data

(60) Provisional application No. 61/135,820, filed on Jul. 24, 2008.

(51) Int. Cl.
*A61F 2/32* (2006.01)
*A61F 2/38* (2006.01)
(Continued)

(52) U.S. Cl.
CPC ...... *A61F 2/30721* (2013.01); *A61F 2/30756* (2013.01); *A61F 2/32* (2013.01);
(Continued)

(58) Field of Classification Search
CPC ............... A61F 2/3603; A61F 2/30756; A61F 2002/30754; A61F 2002/30757;
(Continued)

(56) References Cited

U.S. PATENT DOCUMENTS 3,864,758 A * 2/1975 Yakich ........................ 623/22.13
3,867,728 A * 2/1975 Stubstad et al. ........... 623/17.16
(Continued)

FOREIGN PATENT DOCUMENTS

CN    101500512 A    8/2009
DE    2501080 A1    7/1976
(Continued)

OTHER PUBLICATIONS

English Machine Translation of Hendrik publication DE 103 39 605 A1.*

(Continued)

*Primary Examiner* — Marcia Watkins
(74) *Attorney, Agent, or Firm* — Shay Glenn LLP

(57) ABSTRACT

The disclosure is directed to a resilient implant for implantation into human or animal joints to act as a cushion allowing for renewed joint motion. The implant endures variable joint forces and cyclic loads while reducing pain and improving function after injury or disease to repair, reconstruct, and regenerate joint integrity. The implant is deployed in a prepared debrided joint space, secured to at least one of the joint bones and expanded in the space, molding to surrounding structures with sufficient stability to avoid extrusion or dislocation. The implant has opposing walls that move in varied directions, and an inner space filled with suitable filler to accommodate motions which mimic or approximate normal joint motion. The implant pads the damaged joint surfaces, restores cushioning immediately and may be employed to restore cartilage to normal by delivering regenerative cells.

25 Claims, 9 Drawing Sheets

(51) Int. Cl.

| | | |
|---|---|---|
| *A61F 2/40* | (2006.01) | |
| *A61F 2/42* | (2006.01) | |
| *A61F 2/30* | (2006.01) | |
| *A61F 2/36* | (2006.01) | |
| *A61B 17/56* | (2006.01) | |
| *A61B 17/84* | (2006.01) | |

(52) U.S. Cl.
CPC .............. *A61F 2/3603* (2013.01); *A61F 2/38* (2013.01); *A61F 2/389* (2013.01); *A61F 2/3872* (2013.01); *A61F 2/40* (2013.01); *A61F 2/4202* (2013.01); *A61B 17/562* (2013.01); *A61B 17/842* (2013.01); *A61F 2002/30019* (2013.01); *A61F 2002/30563* (2013.01); *A61F 2002/30576* (2013.01); *A61F 2002/30581* (2013.01); *A61F 2002/30589* (2013.01); *A61F 2002/30594* (2013.01); *A61F 2002/30688* (2013.01); *A61F 2002/30754* (2013.01); *A61F 2002/30757* (2013.01); *A61F 2002/4212* (2013.01); *A61F 2250/0048* (2013.01)

(58) Field of Classification Search
CPC .......... A61F 2002/30761; A61F 2/3872; A61F 2002/30019; A61F 2002/30589; A61F 2250/0048; A61B 17/562
USPC ......... 623/14.12, 16.11, 17.12, 18.11, 22.13, 623/22.14, 22.33, 23.29, 23.3, 23.32, 623/23.39, 23.41, 23.42, 23.43, 22.11, 623/22.12, 22, 21, 24, 22.26, 22.3
See application file for complete search history.

(56) References Cited

U.S. PATENT DOCUMENTS

| | | | |
|---|---|---|---|
| 4,219,892 A * | 9/1980 | Rigdon ............................... 2/24 |
| 4,344,193 A | 8/1982 | Kenny | |
| 4,467,479 A | 8/1984 | Brody | |
| 4,502,161 A * | 3/1985 | Wall ........................... 623/14.12 |
| 4,919,667 A | 4/1990 | Richmond | |
| 4,919,668 A | 4/1990 | Rosenbaum et al. | |
| 4,932,969 A | 6/1990 | Frey et al. | |
| 5,171,282 A | 12/1992 | Pequignot | |
| 5,195,542 A | 3/1993 | Gazielly et al. | |
| 5,344,459 A | 9/1994 | Swartz | |
| 5,383,456 A | 1/1995 | Arnold et al. | |
| 5,441,508 A | 8/1995 | Gazielly et al. | |
| 6,056,777 A | 5/2000 | Mcdowell | |
| 6,110,211 A * | 8/2000 | Weiss .......................... 623/23.11 |
| 6,132,468 A | 10/2000 | Mansmann | |
| 6,193,761 B1 | 2/2001 | Treacy | |
| 6,248,110 B1 | 6/2001 | Reiley et al. | |
| 6,423,083 B2 | 7/2002 | Reiley et al. | |
| 6,482,209 B1 | 11/2002 | Engh et al. | |
| 6,783,546 B2 * | 8/2004 | Zucherman et al. ....... 623/17.16 |
| 7,001,385 B2 | 2/2006 | Bonutti | |
| 7,291,169 B2 | 11/2007 | Hodorek | |
| 7,338,524 B2 | 3/2008 | Fell et al. | |
| 7,491,235 B2 | 2/2009 | Fell | |
| 7,611,653 B1 | 11/2009 | Elsner et al. | |
| 7,670,381 B2 * | 3/2010 | Schwartz .................... 623/17.17 |
| 7,850,983 B2 | 12/2010 | Sevrain et al. | |
| 7,972,380 B2 * | 7/2011 | Linares ....................... 623/14.12 |
| 8,192,491 B2 | 6/2012 | Fox | |
| 8,287,594 B2 | 10/2012 | Cragg et al. | |
| 8,333,805 B2 | 12/2012 | Williams, III et al. | |
| 8,357,203 B2 | 1/2013 | White et al. | |
| 8,361,147 B2 | 1/2013 | Shterling et al. | |
| 8,403,985 B2 | 3/2013 | Hodorek | |
| 8,679,190 B2 | 3/2014 | Myung et al. | |
| 8,771,363 B2 | 7/2014 | Grotz | |
| 8,945,222 B2 | 2/2015 | Linares | |

| | | | |
|---|---|---|---|
| 2002/0143402 A1 | 10/2002 | Steinberg | |
| 2003/0093152 A1 * | 5/2003 | Pedersen et al. .......... 623/14.12 |
| 2003/0163202 A1 | 8/2003 | Lakin | |
| 2003/0220649 A1 * | 11/2003 | Bao et al. ........................ 606/90 |
| 2004/0006393 A1 | 1/2004 | Burkinshaw | |
| 2004/0039450 A1 | 2/2004 | Griner et al. | |
| 2004/0260396 A1 | 12/2004 | Ferree et al. | |
| 2004/0267375 A1 | 12/2004 | Friedrichs | |
| 2005/0171604 A1 | 8/2005 | Michalow | |
| 2005/0182463 A1 * | 8/2005 | Hunter et al. ................. 607/115 |
| 2006/0024076 A1 | 2/2006 | Kato et al. | |
| 2006/0058892 A1 | 3/2006 | Lesh et al. | |
| 2006/0122622 A1 | 6/2006 | Truckai et al. | |
| 2006/0122623 A1 | 6/2006 | Truckai et al. | |
| 2006/0190078 A1 | 8/2006 | Fell | |
| 2007/0016300 A1 * | 1/2007 | Kuslich ...................... 623/17.12 |
| 2007/0078517 A1 | 4/2007 | Engh et al. | |
| 2007/0100461 A1 | 5/2007 | Incavo et al. | |
| 2007/0112428 A1 | 5/2007 | Lancial | |
| 2007/0112458 A1 | 5/2007 | Kondo et al. | |
| 2007/0135920 A1 | 6/2007 | Ferree | |
| 2007/0150067 A1 | 6/2007 | Roger | |
| 2007/0179607 A1 | 8/2007 | Hodorek et al. | |
| 2007/0276491 A1 | 11/2007 | Ahrens et al. | |
| 2007/0288095 A1 | 12/2007 | Wirtel et al. | |
| 2008/0071373 A1 | 3/2008 | Molz et al. | |
| 2008/0200989 A1 | 8/2008 | Cachia | |
| 2008/0234820 A1 | 9/2008 | Felt et al. | |
| 2008/0249638 A1 | 10/2008 | Asgari | |
| 2009/0043344 A1 | 2/2009 | Schlotterback | |
| 2009/0076605 A1 | 3/2009 | Linares | |
| 2009/0187252 A1 | 7/2009 | Howald | |
| 2009/0234453 A1 | 9/2009 | Steinberg | |
| 2009/0259314 A1 | 10/2009 | Linder-Ganz et al. | |
| 2009/0312807 A1 | 12/2009 | Boudreault et al. | |
| 2010/0010114 A1 | 1/2010 | Myung et al. | |
| 2010/0042215 A1 | 2/2010 | Stalcup et al. | |
| 2010/0256758 A1 | 10/2010 | Gordon et al. | |
| 2011/0288642 A1 | 11/2011 | Forsell | |
| 2012/0316645 A1 * | 12/2012 | Grotz ......................... 623/14.13 |
| 2013/0018479 A1 * | 1/2013 | Grotz ......................... 623/22.14 |
| 2013/0096691 A1 | 4/2013 | Myung et al. | |
| 2013/0204377 A1 | 8/2013 | Samuelson et al. | |
| 2014/0257500 A1 | 9/2014 | Grotz | |
| 2014/0316526 A1 | 10/2014 | Grotz | |
| 2016/0058548 A1 | 3/2016 | Grotz | |
| 2016/0095706 A1 | 4/2016 | Grotz | |

FOREIGN PATENT DOCUMENTS

| | | |
|---|---|---|
| DE | 10339605 A1 | 4/2005 |
| EP | 2130517 A1 | 12/2009 |
| FR | 2747914 A | 10/1997 |
| FR | 2803190 A | 7/2001 |
| KR | 20050100511 A1 | 10/2005 |
| WO | WO2004/100839 A1 | 11/2004 |
| WO | WO-2007-125060 A | 11/2007 |
| WO | WO-2008-111073 A2 | 9/2008 |
| WO | WO-2009-052292 A1 | 4/2009 |
| WO | WO-2010-011338 A2 | 1/2010 |
| WO | WO-2010-011388 A3 | 1/2010 |
| WO | WO2010/059098 A1 | 5/2010 |

OTHER PUBLICATIONS

PCT/US10/58977 Search Report and Written Opinion dated Feb. 7, 2011.
PCT/US09/04305 Search Report dated Jan. 19, 2010.
GB0922220.9 Combined Search and Examination Report dated Feb. 11, 2010.
PCT/US11/021674 Search Report dated Sep. 23, 2011.
PCT/US11/021673 Search Report dated Sep. 16, 2011.
PCT/US12/53207 Search Report dated Feb. 14, 2013.

* cited by examiner

RESILIENT ARTHROPLASTY DEVICE

RELATED APPLICATIONS

This application is related to provisional application Ser. No. 61/135,820, filed on Jul. 24, 2008, which is incorporated herein in its entirety and which is relied upon for priority.

BACKGROUND OF THE INVENTION

This invention relates to arthroplasty, and more particularly, to an implant for use in arthroplasty. When hyaline articular cartilage is damaged, it breaks down and joint space is lost. Inflammatory enzymes such as from the Cox-1, Cox-2 and/or 5-Lox systems, are released and loose bodies form adding to the degradation of joint function. Such joint damage is conventionally treated by physical therapy, analgesics, pain medication and injections. When these treatments fail, the traditionally accepted treatment option is arthroplasty implantation or replacing the joint with an artificial joint construct. Current arthroplasty techniques typically use "plastic and metal" implants that are rigid and which ultimately fail due to loosening or infection. Conventional materials for the artificial joint components include chrome-cobalt-molybdenum alloy (metal) and high molecular weight polyethylene (plastic). Each is often fixed by a cement-like mixture of methyl methacrylate to the ends of the bones that define the joint that is the subject of the arthroplasty, or coated with a surface that enables bone ingrowth. Current hip joint replacements typically last about 10-15 years and knee replacements typically last about 5-10 years. Ankle joint replacements, on the other hand, are not very successful, and often fail in the first several years after surgery.

Conditions requiring arthroplasty include traumatic arthritis, osteoarthritis, rheumatoid arthritis, osteonecrosis, and failed surgical procedures.

SUMMARY OF THE INVENTION

The present invention is directed to an orthopedic implant configured for deployment between opposing members of a joint structure that addresses many of the shortcomings of prior artificial joints. The arthroplasty implants embodying features of the invention are configured to preserve joint motions while removing the pain and dysfunction following the development of arthritis or joint injury. The arthroplasty implant in accordance with the present invention achieves improved physiologic motion and shock absorption during gait and acts as a resilient spacer between moving bones during limb movement. The combined characteristics of the implant include anatomic design symmetry, balanced rigidity with variable attachment connections to at least one of adjacent normal structures, and durability which addresses and meets the needs for repair or reconstruction thus far missed in the prior art. The implant should be secured to at least one of the bones of the joint structure.

More specifically, the resilient implant embodying features of the invention has a first wall configured to be secured to a first bone of the joint structure by one or more appendages such as a skirt or one or more tabs and a second wall configured to engage a second and usually opposing bone of the joint structure. A side wall extends between the first and second walls of the implant and together with the first and second walls preferably defines at least in part an inner chamber or space between the first and second walls. The implant is configured to provide linear or curvilinear and/or rotational motion between the first and second bones which mimics or approximates the natural motion between these bones. The inner chamber or space is configured to maintain a filler material therein such as an inflation fluid or a resilient material and preferably to maintain spacing and provide support between the interior of the first and second walls to avoid significant contact therebetween. The walls of the implant are preferably sealed about the periphery thereof to maintain the interior chamber in a sealed condition to avoid loss of inflation fluid or filling media. The side wall or walls may be formed from the edges or periphery of the first and second walls. The properties of the implant walls and the interior are controlled to provide the particular resiliency desired for the joint in which the implant is to be placed as well as any desired motion between the first and second walls. A conduit may extend from a source of inflation fluid or other filling medium to the interior of the implant to facilitate expansion of the implant after deployment within the joint. The inflation fluid may be a gas, a liquid, a gel or a slurry, or a fluid that becomes a suitable resilient solid such as a curable polymer. Selection of the inflation or interior filling medium may depend upon the nature of the joint structure in which the implant is to be deployed, its anatomy, pathophysiology, and the properties of the implant material.

There may be several alternative embodiments depending upon the site in which the implant is to be deployed. For example, the polymer forming the side wall may be semi-compliant or elastic and the inflation fluid may be incompressible (e.g., a liquid). Alternatively, the polymer forming the side wall may be non-compliant (non-elastic) and the inflation fluid or filling medium may be compressible, e.g., a gas or a resilient polymeric foam or sponge-like solid that may have a closed cell structure. The first and second walls of the implant need not have the same properties as the side wall. For example, parts of the implant such as the side wall portion may be compliant and the first and second wall portions in contact with the bone or other joint structure may be non-compliant. Additionally, the various walls or portions thereof may also be reinforced with non-compliant or semi-compliant polymer strands, beads or gel coating such as biologic or polymer latticework. The thicknesses of the first, second and side walls may be varied to accommodate for the needs of the joint structure from the standpoint of strength, elasticity and wear resistance. Moreover, the walls of the implant may be provided with joint tissue regeneration agents that rebuild the joint structure in which the implant is deployed. The regeneration agent may be incorporated into the wall of the implant prior to delivery or placed between the surface of the implant and the joint structure which it contacts after delivery. All or part of the walls of the implant may also be made of a biodegradable polymer, by minimally manipulated autograph, allograph or xenograph tissues, or a combination thereof. The method of surgery may incorporate a progressive application of the implant embodiments depending upon clinical needs.

The implant is preferably formed of suitable biocompatible polymeric materials, such as Chronoflex, which is a family of thermoplastic polyurethanes based on a polycarbonate structure (Al, the aliphatic version, Ar, the aromatic version and C, the casting version) available from Advan-Source Biomaterials, Corp. Other polymers include Bionate 80, 90A, 55 or 56, which are also thermoplastic polyurethane polycarbonate copolymers, available from PTG Medical LLC., an affiliate of the Polymer Technology Group located in Berkeley, Calif. Other commercially available polymers include Purisil 20 80A which is a thermoplastic silicone polyether urethane, Carbosil 20 90A which is a thermoplastic silicone polycarbonate urethane and Biospan which is a segmented polyurethane. These polymers are available as tubing, molded or dipped components, solution, pellets, as a casting and as a cast film for the side and first and second walls. The implant may be formed by casting, blow molding or by joining sheets of polymeric material by adhesives, laser welding and the like. Other methods of forming the implant may also be suitable. The walls may also be provided with reinforcing strands which are located on the surface of the walls or incorporated within the walls. The implant material should be biocompatible, non-toxic, and non-carcinogenic and should be resistant to particulation.

The present invention provides an improved joint implant which is designed to endure variable joint forces and cyclic loads enabling reduced pain and improved function. Depending upon the particular joint involved there may be linear or curvilinear motion between the first and second walls, rotational motion between the first and second walls or both linear and curvilinear motion and rotation motion between the first and second walls. Preferably, a space is maintained between the inner surfaces of the first and second walls to avoid erosion and wear therebetween.

The resilient arthroplasty implant embodying features of the invention is preferably deployed as a minimally invasive procedure to deliver the implant into a prepared space in a preselected joint structure, where upon it is inflated to create a cushion, to cover damaged or arthritic cartilage and to be employed to deliver stem cells or living chondrocytes or other tissue regeneration agents. The goal of such deployment is to reduce pain and improve function, to reverse arthritis, to fill in osteochondral defects succinctly, thereby avoiding living with both dysfunctional and ablative metal/plastic prostheses or the pathophysiologic state necessitating the procedure. The operative plan is simple, systematic, and productive of new joint space with regrowth potential involving joint debridement by routine arthroscopic methods or steam application, followed by implantation of the implant. The implant provides three things, namely a covering or patch for the damaged or worn joint surface, an inflated cushion to pad gait as in normal walking in the lower extremity, and delivery of regenerative cells on the cartilage remnant surface. The stem cells may be injected as the implant is being expanded and/or directed into the adjacent hyaline cartilage via an implant coating or perfused cell template. Viscolubricants such as Synvisc or Hyalgan, analgesics such as Lidoderm, anti-inflammatory and/or antibiotic coatings as well as those stimulating cell growth may accompany the composite external implant. The implant is left in place as long as feasible, at least until regenerative cells can attach to the adjacent natural joint surface (usually in about 24 hours), or until wound healing (which may take up to 28 days or more depending on the joint structure). Preferably, the implant is designed stay within the joint structure for years, providing inert padding, cushioning and a new cell source. The implant may be used in weight bearing and non-weight bearing interfaces. Animal usage of the implant, such as in horses and dogs, will benefit following hip and knee injuries. The implant is intended primarily for mammalian use.

These and other advantages of the invention will become more apparent from the following detailed description and the attached exemplary drawings.

DETAILED DESCRIPTION OF EMBODIMENTS OF THE INVENTION

The present invention is directed to arthroplasty implants and procedures for a wide variety of joints such as, for example, hips, knees, shoulders, ankles, elbows, wrists, fingers, toes, temporomandibular joints and the like, but for clarity, as well as brevity, the discussion herein will focus on an implant for a hip joint and an implant for replacing the talus bone of a patient's ankle.

Figure 1:
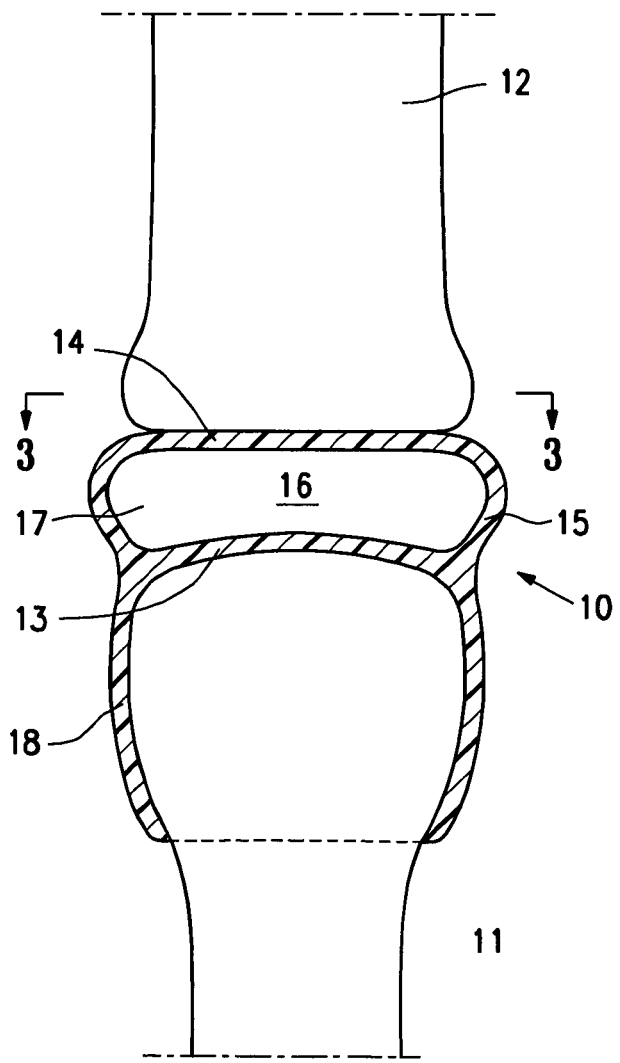
FIG. 1 is a schematic cross-sectional view of an idealized joint structure having first and second bones with an implant having features of the invention disposed within the space between the opposing bones of the joint structures.

FIG. 1 is a highly schematic idealized view of an implant 10 embodying features of the invention that is deployed within a joint structure having a first bone 11 and a second bone 12. The implant 10 has a first wall 13, a second wall 14, and a side wall 15 which define the implant interior 16 which contains filling material 17. The first wall 13 is secured to the end of the first bone 11 by the skirt 18 that extends from the first wall 13 and the second wall 14 engages the end surface of the second bone 12 and may also be secured thereto. The side wall 15 extending between the first and second walls 13 and 14 defines at least in part the implant interior 16 which is filled with filling material 17. The inner surfaces of wall 13 and skirt 18 preferably conform to the particular surface of the head of the patient's first bone 11. The outer surface of the second wall 14 is preferably configured to conform to the end surface of the second bone 12. The drawings are highly schematic and do not depict details of the joint surface features such as of the end of the first bone 11 or the end of the second bone 12, since human pathology and variation reflects both the patient's immediate and evolving pathophysiology.

The edge of the implant 10 shown in FIG. 1 has a depending skirt 18 to secure or anchor the implant to the end of bone 11, but may have one or more depending tabs that may be employed for similar functions as will be discussed in other embodiments. The skirt 18 (and/or tabs) may tightly fit about the end of the first bone 11 as shown, or the skirt can be secured by adhesive (e.g. methyl methacrylate, bone ingrowth) to the supporting bone structure or be mechanically connected by staples, screws and the like. Moreover, the lower portion of the skirt 18 may be secured by a purse string suture or a suitable strand (elastic or tied) that is tightly bound about the outside of the skirt.

Figure 2:
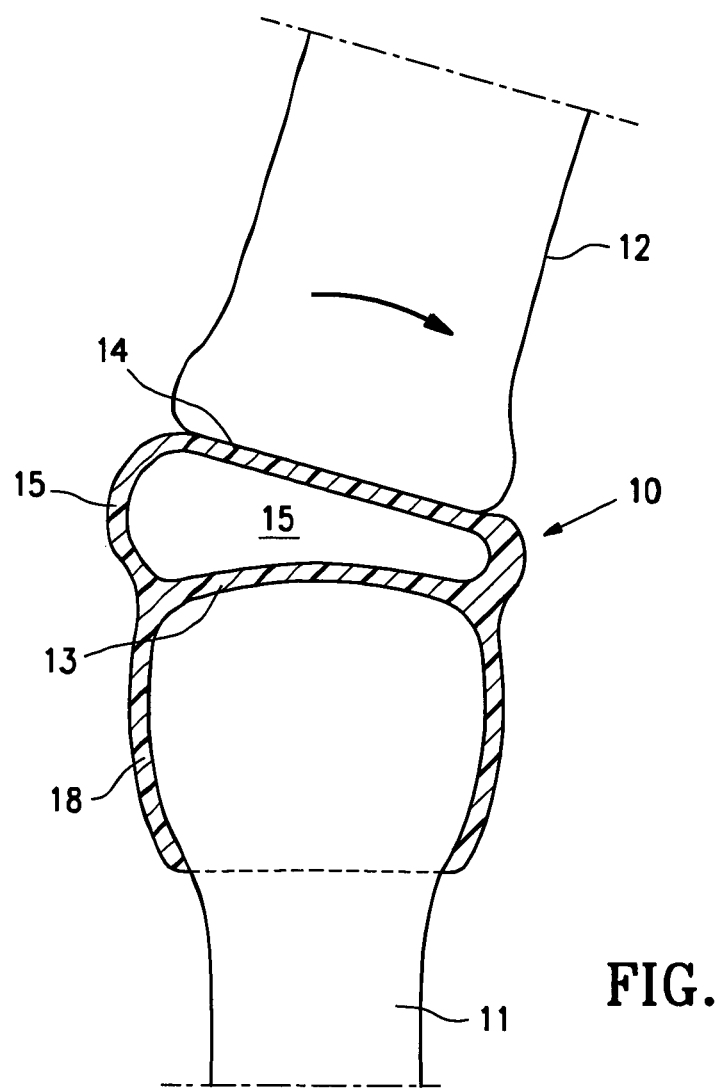
FIG. 2 is similar to FIG. 1 illustrating curvilinear movement between the two opposing bones.
Figure 3:
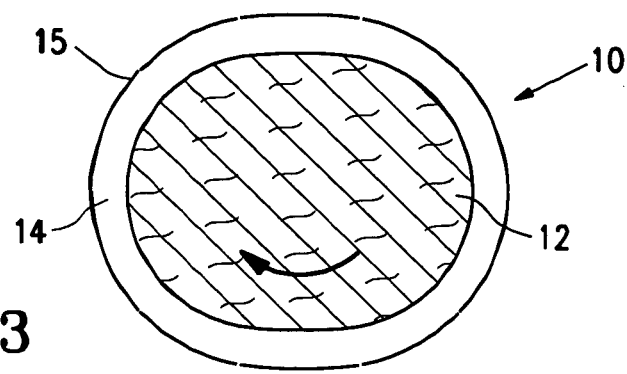
FIG. 3 is a transverse cross sectional view taken along the lines 3-3 in FIG. 1 illustrating rotational movement between the two opposing bones.

As shown in FIG. 1, the implant interior 16 between the wall 13 and the wall 14 is filled with filler material which aids in maintaining the desired implant dynamics within the joint structure. The nature of the filler material such as a fluid and the characteristics of the walls 13, 14 and 15 may be selected to maintain a desired spacing between the walls in order to accommodate the pressure applied by the bones of the joint structure to the implant 10 and to allow suitable motion between the first and second walls 13 and 14 of the implant 10 which facilitate bone motion which mimics or approximates normal movement for the joint members involved such as shown in FIGS. 2 and 3. Alternatively, as mentioned above, the inner chamber may be filled with resilient material to provide the desired spacing, pressure accommodation, while allowing desired physiologic motion between implant layers. The implant 10 is preferably configured to be shaped like the joint space and bone surfaces being replaced or to fill the void produced by injury or disease so that the natural joint spacing and cushioning of the joint interface is restored toward normal physiologic appearance and function. Fluids such as saline, mineral oil and the like may be employed to inflate the implant.

Linear or curvilinear movement between the first and second walls 13 and 14 as a result of movement of the first and second bones 11 and 12 is illustrated by the arrow shown in FIG. 2. Rotational movement about the bone axis between the first and second walls 13 and 14 as a result of axial rotation between the first and second bones 11 and 12 is illustrated by the arrow shown in FIG. 3. While not shown in the drawings, there may be slippage between the second bone and the second wall in addition to wall movements within the implant per se to provide desired joint movements. The skirt 18 is designed to secure the general implant to the joint structure so as to avoid dislocation of the implant. Movement of the joint with the implant 10 in place will be a shared function of both the moving opposing walls 13 and 14 of the implant but also a function of the movement of the wall 14 which may be less attached to the joint members. There may be slight movement between the skirt 18, wall 13 and the first bone 11. As shown in FIG. 2 one side of the side wall 15 is in compression and the other is stretched to accommodate bone interface movement. The walls 13 and 14 may be thicker is some areas to accommodate particular loads and the side wall 15 may be thinner and more elastic to accommodate rolling and stretching thereof.

The interior 16 of implant 10 is adjustably filled by the physician from an appropriate source thereof after the implant is deployed to ensure that the pathologic joint space becomes a resilient cushion again which aids restoration of worn or damaged cartilage interfaces in the joint by covering cartilage defects with the implant material, cushioning the joint and defects therein and delivering cell regeneration agents. In one embodiment, the arthroplasty implant comprises a bio-compatible inflatable member that is filled with a biocompatible fill material such as a gas, liquid, gel or slurry, or fluid that becomes a resilient solid to provide relative movement between the first and second walls 13 and 14. The filling or inflation media may be inserted through an injection valve site leading to the cannula which delivers the material into the interior of the implant. In an alternative embodiment, the implant may be filled with or have an interior formed of biologically compatible resilient material, e.g. a closed cell sponge filled with suitable fluid that is inserted into the interior of the implant prior to the implant's deployment or injected into the interior after the implant is deployed at the joint site. The interior of the implant may be provided with lubricious material to facilitate movement between the inner wall surfaces and to minimize contact wear therebetween. The polymeric walls of the implant may be impregnated with or otherwise carry tissue regeneration agents such as stem cells, living chondrocytes, and/or genes to repair joint surfaces.

The implant can be used in a variety of joints where the implant replaces a bone on bone surface and cushions the interaction between the articular ends of any two bones, such as at the femoral-acetabular interspace of a patient's hip, the humerus and glenoid scapular component in the shoulder, the femoral tibial and patella femoral knee interfaces, the replacement of talus bone in the human ankle between the tibia and calcaneus and the like. Where the implant is substituting or enhancing articular cartilage, the rigidity can be reduced or enhanced to maximize conformation changes that arise during motion as enabled by the two opposing walls and intended inner space, coupled with considerations in any joint surgical reconstruction with accommodation to or amplification of the existing joint ligaments, tendons or dearth thereof. The implant 10 may be deflated and removed by minimally invasive surgery, for example after the implant has served its purpose of regenerating tissue or if another clinical condition warrants its removal. However, it may not be clinically necessary to remove the implant even if inflation is lost, since the two remaining functions of patching the injured cartilage, and delivering restorative cells may justify implant retention.

Figure 4:
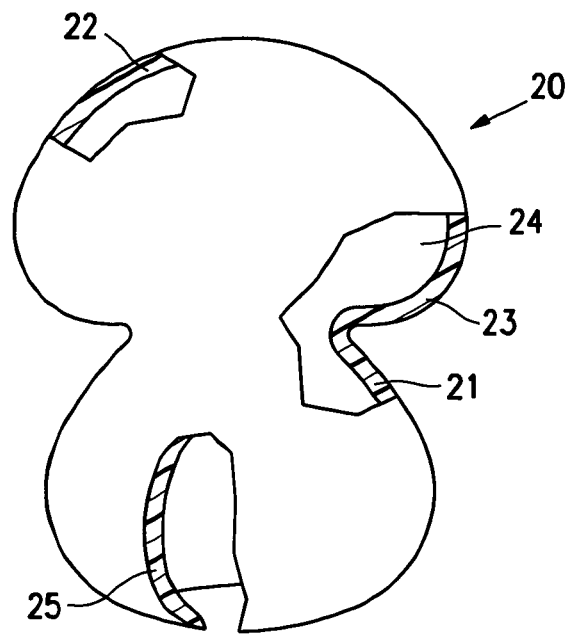
FIG. 4 is a perspective view, partially in section, of an implant embodying features of the invention with an enlarged upper portion prior to implantation.
Figure 5:
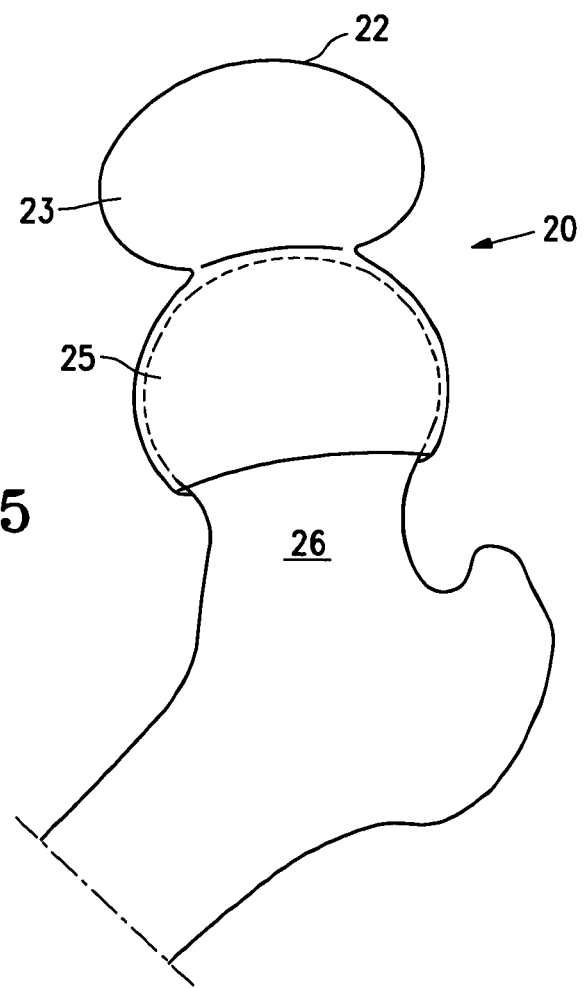
FIG. 5 is an elevational view of the implant shown in FIG. 4 mounted on the head of a patient's femur.
Figure 6:
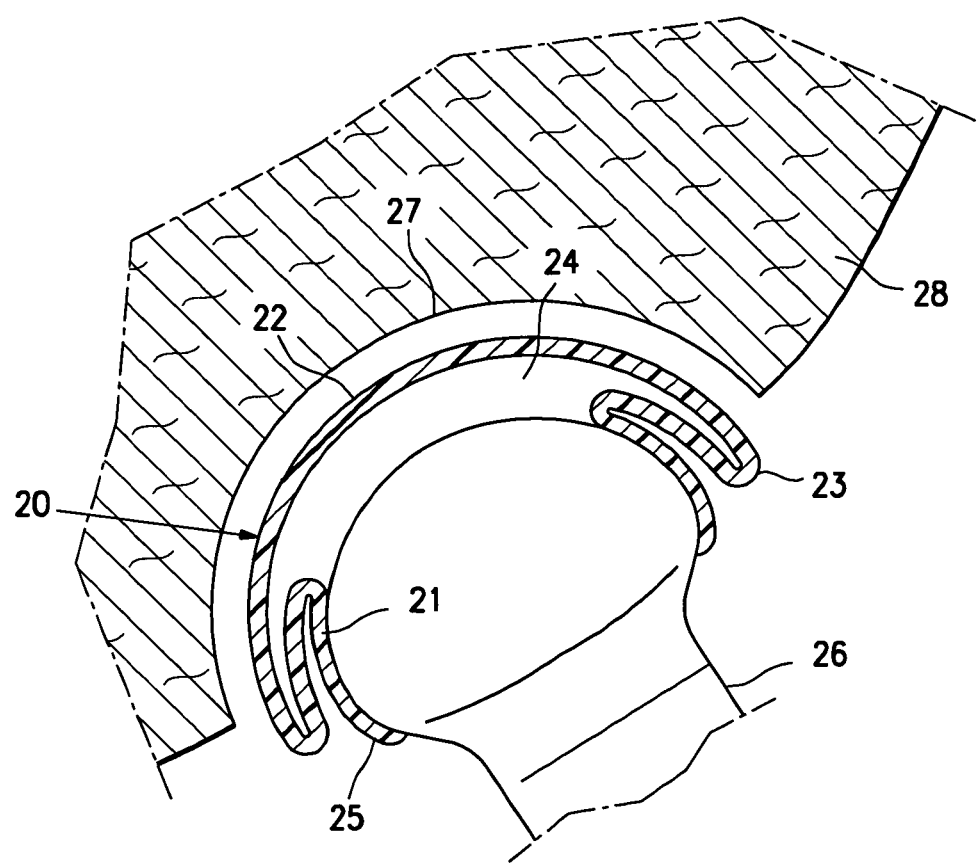
FIG. 6 is a cross-sectional view of the implant shown in FIGS. 4 and 5 deployed between the head of a patient's femur and acetabulum after release of traction to allow for the bones to settle into their natural albeit pathologic angles of repose.

FIG. 4 is a perspective view, partially in section, illustrating a hip implant 20, similar to that shown in FIG. 1, but with a much larger upper portion. The large upper portion of the implant 20 has a first wall 21, a second wall 22 and a side wall 23 which define at least in part the interior 24. Skirt 25 depends from the first wall 21 and secures the first wall 21 to the end of the patient's femur 26 as best shown in FIGS. 5 and 6. FIG. 6 illustrates the implant mounted on the head of the femur 26 with the second wall 22 of the filled upper portion configured to engage the corresponding acetabulum 27 of the patient's pelvic bone 28. The skirt 25 surrounds the head of the patient's femur 26 and secures the implant 20 thereto. In this embodiment, the enlarged upper portion of the implant creates overlapping layers. The overlapping layers are directed in opposite directions relative to the interior portion of the implant such that an overlapping layer is directed towards the interior portion and an overlapping layer is directed away from the interior portion of the implant, like a redundant membrane, in the side wall 23 between the first and second walls 21 and 22 to accommodate the normal movement of the first or second. This provides greater motion between the femur and the acetabulum and also provides implant stabilization over the head of the femur 26. This structure also accommodates variation in individual joints that occur from patient to patient.

In the embodiment shown in FIGS. 4-6 the first wall 21 does not extend across the entire end of the patient's femur as in the embodiment shown in FIGS. 1-3. However, the implant 20 may be designed so that first wall 21 may extend over the head of the femur as shown in FIGS. 1-3 (and FIGS. 7-12 discussed hereinafter). The second wall 22 and the side wall 23 tend to roll as the femur 26 moves within the acetabulum 27.

Prior to deploying the implant embodying features of the invention, the cartilage lining the joint is prepared by removing hyaline or fibro cartilage flaps or tears, and areas of chondral advanced fissuring are excised or debrided to create precisely defined defects surrounded by stable normal remnant hyaline cartilage with vertical edges in relation to the damaged surface. It is these defects of the cartilage previously normal surface into which new living cells may be injected or otherwise inserted, and allowed to aggregate by the implant interpositional arthroplasty proximate expanded compressive external wall material. Synovitis invading the joint periphery may be vaporized and extracted conventionally or by the use of steam. Areas of greater cartilage damage are removed for subsequent regeneration and the less afflicted areas having stable cracks are treated to seal or weld the cracks. Areas where the tugor or consistency or minimally damaged cartilage can be preserved are intentionally saved rather than destroyed so as to support the normal spacing and gliding opportunity of the more normal joint interface. Thus, normal cartilage is left behind and abnormal cartilage is removed with the implant making up for the deficiencies. With the present invention, it is preferred to avoid joint dislocation so as to preserve natural innervations and vascularity and thus preserving the blood supply afforded by the medial and lateral circumflex arteries for the hip joint to the femoral head.

Joint preparation is usually performed under a brief general anesthetic of outpatient surgery. A muscle relaxant combined with traction (e.g. 60 pounds force for a hip implant) opens the joint wider to permit improved visualization for joint preparation and implant installation, increasing the space between the remnant cartilage from about 3 up to about 12 mm. Increasing the space allows the surgeon to wash out noxious enzymes, to remove invasive synovitis, to remove loose bodies, to prepare osteochondral defects ideally and otherwise prepare the joint for the implant. Partial or complete inflation of the implant will usually precede release of traction. Regeneration agents or cells are inserted with the implant or as a fluid or 3-D template prior to release of traction and wound closure. It is preferred to perform joint debridement, implant deployment and application of cell regeneration agent, e.g. stem cell application, under the same anesthetic. As described by several companies in the Stem Cell Summit held in New York, N.Y. on Feb. 17, 2009, it is desirable to obtain an aspiration of the patient's bone marrow from the iliac crest after anesthesial sterilely at the beginning of the operation. The intraoperative technologist will "dial in the cells" to regenerate areas of maximum pathophysiology while the surgeon debrides or otherwise prepares the joint and inserts the implant, placing the cells at the best time. Cell implantation may also occur as a secondary or tertiary reconstructive treatment adjunct.

Figure 7:
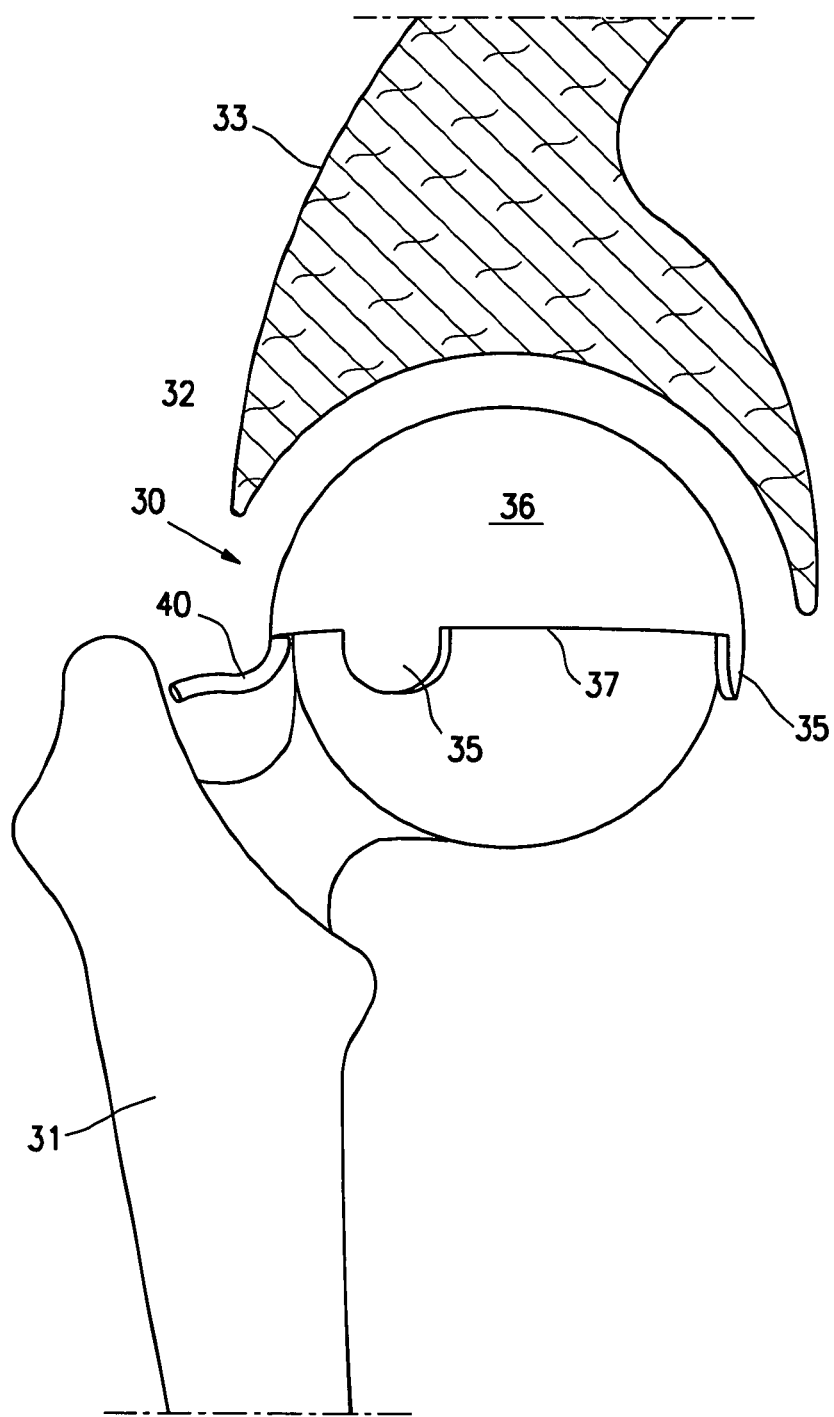
FIG. 7 is an elevational view of a resilient arthroplasty implant with a smaller upper portion than that shown in FIGS. 4-6 that has been deployed between the head of patient's femur and the acetabulum of the pubic bone.
Figure 8:
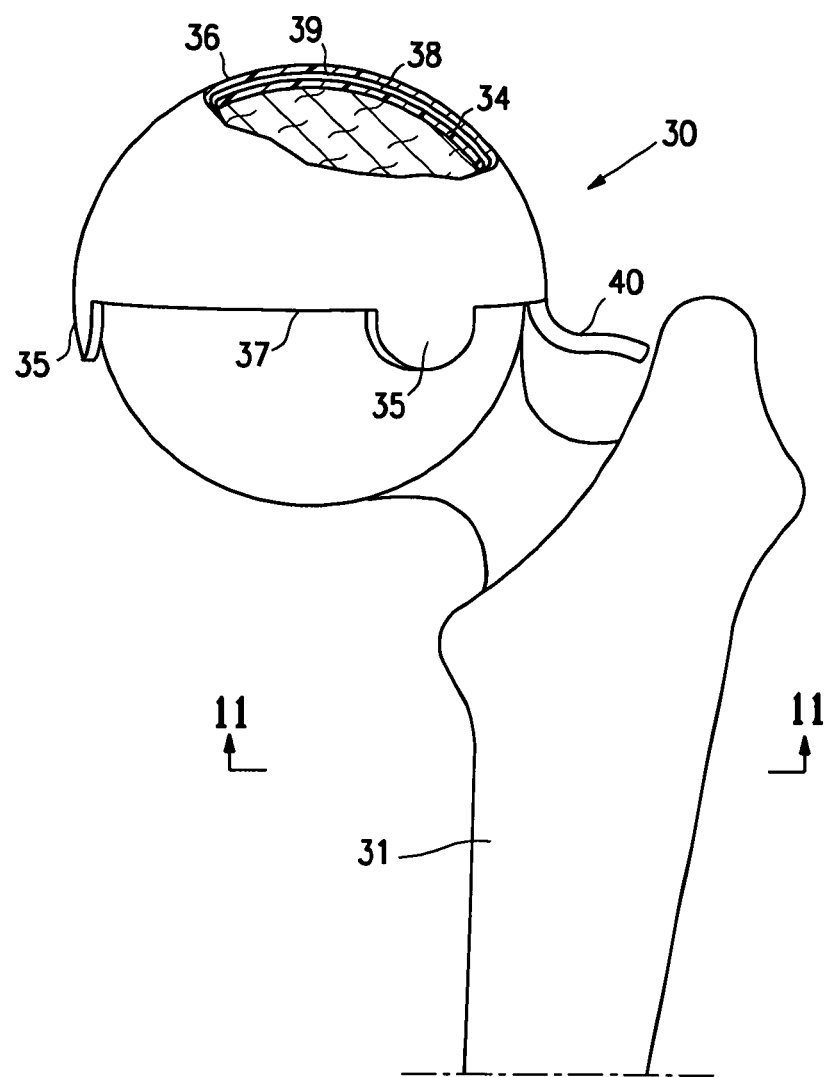
FIG. 8 is an elevational anterior view of a left proximal femur with an implant placed over the femoral head portion of the hip joint as shown in FIG. 7, in partial cross section, to illustrate details thereof.
Figure 9:
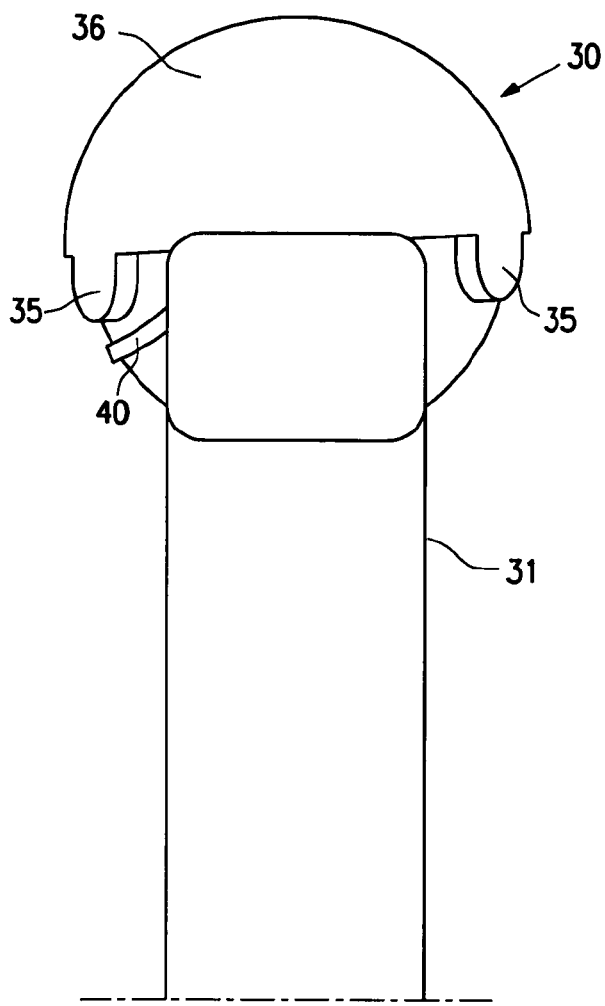
FIG. 9 is a lateral elevational view of a femur with the implant shown in FIG. 6, as viewed from the "side of the body" or lateral hip aspect.
Figure 10:
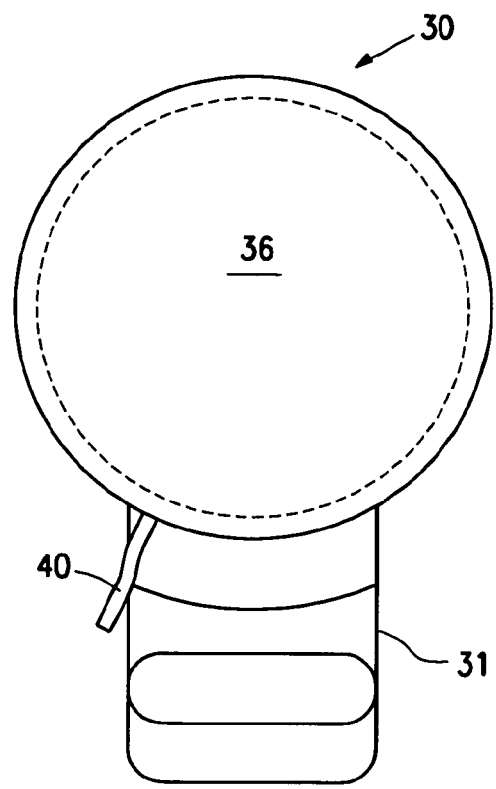
FIG. 10 is a superior view of a femur with the implant shown in FIG. 7.
Figure 11:
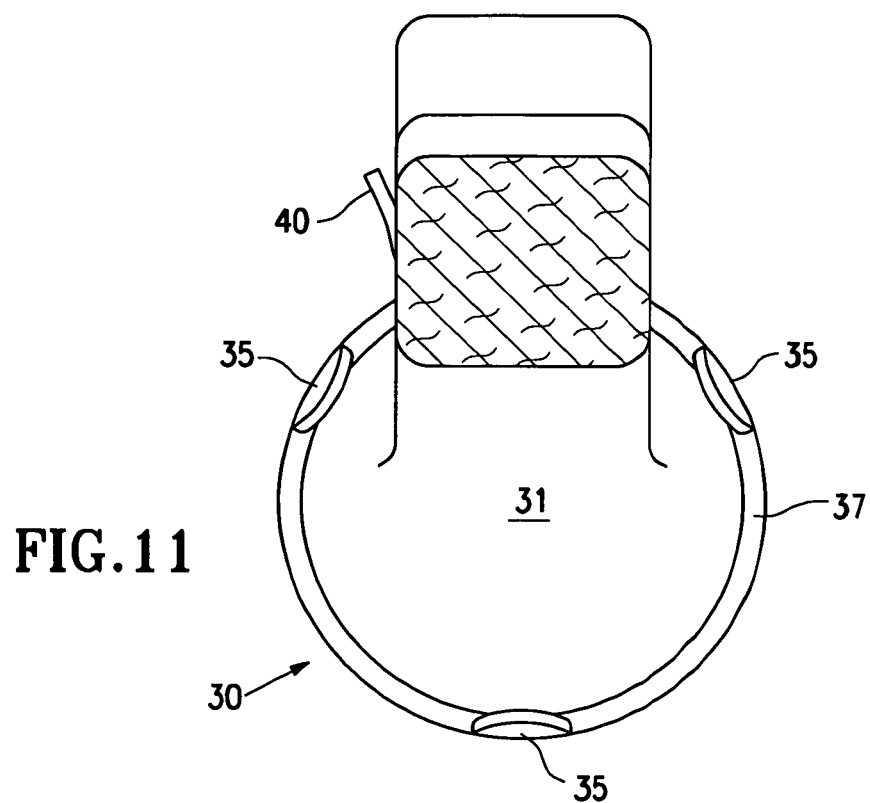
FIG. 11 is an inferior view of the hip joint invention iteration or implant in FIG. 10.

FIG. 7 is an elevational view, partially in section, of an alternative resilient implant 30 deployed within a patient's hip structure comprising the head of the patient's femur 31 and the acetabulum 32 of the patient's pelvic hip bone 33. The upper portion of the implant 30 is smaller than that shown in FIGS. 4-6. Details of the interior of the joint are not provided such as cartilage, ligaments and the like for the purpose of clarity. The resilient implant 30 embodying features of the invention is disposed within the space between the femur 31 and the acetabulum 32. FIGS. 7-11 illustrates the implant 30 mounted on the head of femur 31 without the pressure from the acetabulum 32 for purposes of clarity.

The implant 30 shown in FIGS. 7-12 is shaped like a half an orange rind or a hemisphere for a hip joint. The implant 30 has a first wall 34 seen in FIG. 8 which is secured to the head of the femur 31 by a plurality of depending tabs 35. The tabs 35 may be attached to the femur 31 by a suitable adhesive or mechanically such as by a screw or pin. The second wall 36 of the implant engages the acetabulum 32, but it also may be provided with tabs and the like for securing the second wall the acetabulum 32.

The side wall 37 extends between the first and second walls 34 and 36 to form an interior 38 which receives filling material 39 through tube 40. The implant 30 would also be appropriate for the humeral head in the shoulder or one condyle of the knee or of the humerus, but other shapes may be desired for other joint configurations whether relatively flat as in the thumb base, or more inflated toward a ballooning construct as in the ankle when the talus bone is collapsed. In many embodiments the implant 30 is a weight bearing spacer that will allow joint motions to approach normal, whether filling the space left by an entirely collapsed peripheral joint bone or the space of ablated cartilage proximate surfaces diffusely as in osteoarthritis or succinctly as in osteonecrotic defects or localized trauma. The walls 34 and 36 may be used as a membrane for holding living cells in proximity of the osteochondral defect long enough for the cells to attach (e.g. 24 hours) or to deeply adhere (up to 28 days) or return to normal (up to one year). Weight bearing will be expected to increase as distal lower extremity joints are treated.

Figure 12:
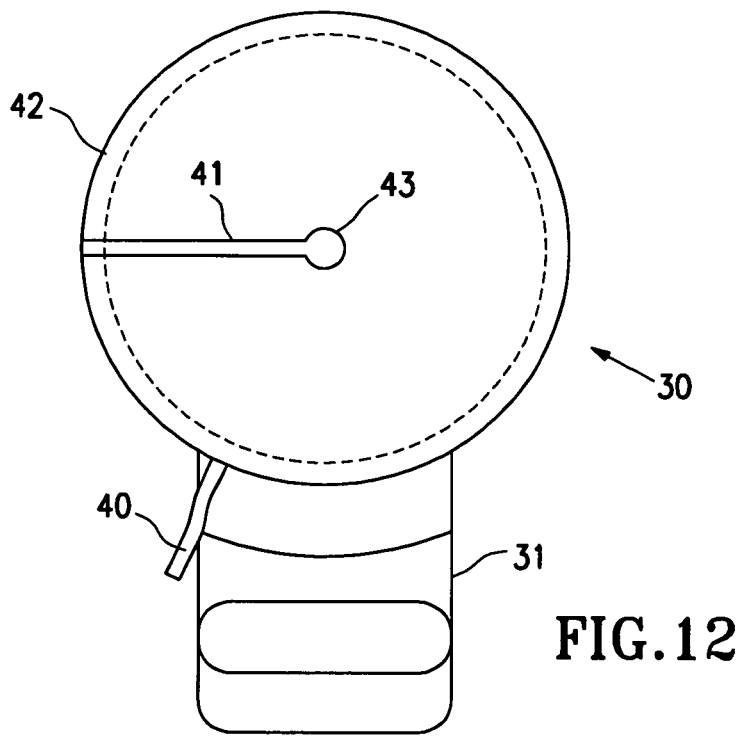
FIG. 12 is a superior or cephalad view of a patient's hip with a resilient implant having features of the invention, viewed from the head of the patient or from a cephalad to caudad direction.

Motion is believed to be primarily between the spaced walls of the implant peripherally secured to joint structures, although some motion may occur between the implant and the joint surfaces (as with current bipolar hip hemiarthroplasties). As shown in FIG. 12, the implant 30 may be provided with a slot 41 extending from the periphery 42 of the implant to a centrally located passage 43 through the implant to accommodate the ligament of the head of the femur for hip implants. Knee implants (not shown) may have two slots leading to separate passages for receiving the anterior and posterior cruciate ligaments. Implants for other locations may have similar variable structures to accommodate anatomical features. Implant walls 34 and 36 should have sufficient inherent flexibility to mold to the existing deformities imposed by either natural ligament, bone, tendon and remaining cartilage deformities of the internal joint space filled as a cushion. The wall exteriors may be flat or formed with random or specific patterns for purposes of glide or trends for traction against adjacent surfaces, or as sulci or venues for cell delivery materials.

A separate portal or tube (not shown) or the existing conduit 40, may be used to extract noxious inflammatory enzymes that can be aspirated at appropriate clinical intervals. Inflammatory enzymes in the COX1, COX2 and or 5LOX pathways can be extracted. Viscolubricants can be injected into the interior of the resilient arthroplasty device through existing conduit 40 or through a long needle to aide in distension, expansion, lubrication (with predetermined microporosity).

Figure 13:
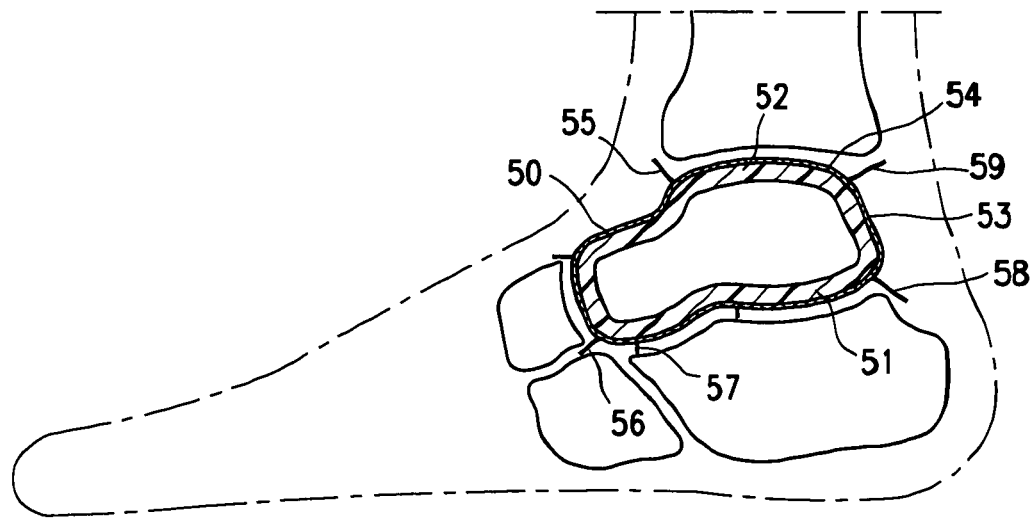
FIG. 13 is a lateral view of the patient's ankle having a resilient arthroplasty device implant which embodies features of the invention between opposing joint structures.
Figure 14:
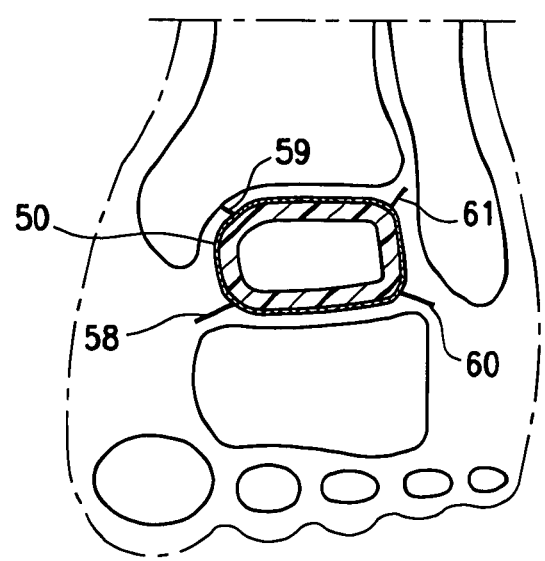
FIG. 14 is a mortise (30 degree oblique AP) view of the patient's left ankle with implant shown in FIG. 13.

The ankle version of the arthroplasty implant 50 of the present invention shown in FIGS. 13 and 14 has basically a square transverse cross-section that must take into account supratalar ankle dorsi/plantar flexion, subtalar eversion/inversion motions, ligament fixation-needs, and the accommodation to existing bony architecture as implant variables accounting for the ipsilateral joint pathophysiology. The implant 50 has a first wall 51, a second wall 52 and a side wall 53 which extends between the first and second wall. The exterior of the implant 50 may have a mesh material 54 with a plurality of chords 55-61 for securing the implant 50 to adjacent bones or to remnant ligaments which are attached to adjacent bones.

The implant 50 may be inflated with gas and/or liquid to open wider the space between the tibia above and the calcaneus below to accommodate collapse of the talus bone as in the flattening which succeeds talus fracture with avascular necrosis, or it may be filled with a liquid that becomes a resilient solid. The instant center of the implant's rotation will be constantly changing, with the talus implant mainly stable and with the tibia moving over it. Deformation with weight bearing during the average human's. 10,000 daily steps or 2-4 million annual gait cycles required by the stance and walking of normal activities of daily living, must be balanced between sufficient solidarity of the implant to maintain axial load, avoiding circumferential stress, and shear forces imposed by the tibia distal plafond on the dorsal ankle implant allowing stance and gait of the patient while avoiding implant migration or failure. Further accommodation to lateral forces imposed by the boney medial and lateral malleoli, need to be endured through the cyclic load of walking, while collapsing with enough give to absorb shock and to match the shape of surrounding structures of bone and ligament tissue. Whereas the axial load between the distal tibia through the talar implant to the dorsal calcaneus will be loaded during stance and especially while walking on a level plane for supratalar motion, the lateral forces will be loaded particularly with subtalar motion while walking on an uneven plane or with inversion/eversion.

The dimensions of the various implant walls will vary depending upon the material properties thereof as well as the needs for a particular joint. Additionally, the first and second walls may require a thickness different from the side wall. Generally, the implant may have a wall thicknesses of about 0.125 mm to about 3 mm, preferably about 0.5 mm to about 1.5 mm. The spacing between the first and second wall within the interior can vary from about 0.5 mm to about 5 mm for most joints (except for the implant for an ankle when an entire collapsed bone space is being replaced), preferably about one to five centimeters to fill between the tibia and calcaneus. In the ankle invention version of the implant, the amount of inflation of the implant per se will be directly proportional to the amount of talus bone collapse between the distal tibia and proximal calcaneus—thus as much as 5 cm implant distension or expansion may be required to be maintained between superior and inferior surfaces in FIG. 13 of the talus, while as much as 10 cm anterior and posterior expansion may be required for the ankle implant between the posterior soft tissues such including the Achilles tendon and the anterior navicular bone as relates to the talus as seen in FIG. 13.

The method of insertion for the hip joint invention will be a minimally invasive approach, ideally arthroscopically facilitated, as long as the surgical timing and result quality permit smaller incisions. The hip patient will be placed in the lateral decubitus position (lying non-operative side down on the operating table) with a stabilizing operating table pole and pad apparatus positioned to fix the pelvis. The external stabilizing table and attachments will include a padded metal pole beneath the pubis or pelvic bone from posterior to anterior, along with other external anterior and posterior pelvic stabilizing paddles. The affected leg will be attached beneath the knee with a distracting mechanism that applies about 60 pounds of distal force to open the hip joint about 1 cm once the patient is under general anesthesia. The hip joint is arthroscopically debrided through at least one anterior 0.5 cm incision and one posterior 0.5 cm incision, to remove from the femoral head acetabular (ball and socket) joint arthritic debris such as synovitis, loose bodies and noxious inflammatory enzymes. In certain cases a larger open incision may be needed. A smoothing or electronic/ultrasonic/steam or other chondroplasty method may be performed to make the remaining cartilage smoother to better accommodate the hip implant, and protuberant osteophytes or lateral bone overgrowths may be arthroscopically removed or if needed by open excision. A lateral hip incision may be required between 2 and 10 centimeters in length to deal with deformities and/or to insert the implant. In cases of major deformities appropriate reconstruction will add to the basic procedure.

Once the joint is open and cleared, the hip implant will be inserted laterally and fixed via the skirt or tabs to the adjacent structures including the peripheral femoral head and/or acetabular rim. Preferably, the implant is inserted arthroscopically through a cannula about 10 mm in diameter with the implant in the deflated construct, and once inside the prepared joint space and secured therein by the skirt or tabs, the implant will be distended or inflated with gas, gel, fluid or fluid that becomes a resilient solid to fill the original natural space of about 0.5 cm between the upper acetabulum and lower femoral head, covering as much of the upper hip joint as required as the implant expands to fit the space. Tensioning will be by the surgeon's sense of proper pressure application aided by a gauged syringe for insertion of viscolubricants such as Synvisc, Hyalgan, Supartz and/or analgesics such as lidocaine gel. The insertion of liquids to the joint per se may be directly, through a cannula to the joint space previously in place for debridement, and or via a cannula or tube that is not part of the original implant assembly. Once the joint is cleaned, the implant is inserted and appropriately fixed to avoid extrusion or dislocation thereof. This may be via attachment of the implant tabs and/or by a combination of tab use plus intended friction created by implant surface coverings (analogous to Velcro) or a draw string at the smaller base of the implant.

The walls of the implant embodying features of the invention may be composite structures. For example, the innermost layer may be impervious to preclude escape of inflation or other filling media, a central layer may be porous or otherwise contain treatment or cell regeneration agents, and the outer layer may be a thin, but strong layer of a thermoplastic such as a thermoplastic polyurethane which has microporosity sufficient to allow passage or egress of treatment or cell regeneration agents from the central layer. The degree of microporosity to enable egress of treatment or cell regeneration agents from the central layer is found in polymer layers such as Chronoflex or Bionate 55. The external wall of the implant may be coated and/or impregnated with a latticework of polymer surface sprayed or layered on the outside of the implant to promote cartilage tissue regeneration. This most external surface coating may contain living chondrocytes as in the Carticel procedure by the Genzyme company, and/or may contain stem cells with directed gene mutations to enhance adherence of the coating to the implant. The living cells may be imposed in between troughs while the surface areas of prominence may be used for space validation, traction, and cell protection.

The implant embodying features of the invention may be used in a series of treatments wherein the first treatment involves use of autologous or minimally manipulated allograft interpositional tissues or xenograph, the second treatment involves the use of the same type of tissue added to stem cells or chondrocytes and the third treatment involving deployment of the implant if the first two fail or are ineffective.

The implant may be provided with latticework or other reinforcing strands, preferably on the exterior or within the wall thereof to control the maximum expansion of the implant when deployed at the orthopedic site.

The method of insertion of the ankle implant generally will be through an anterior surgical ankle approach or tendon separating incision from the distal tibia to the proximal talus (or calcaneus if the talus is absent), removing and reconstructing portions of the superior and inferior ankle extensor retinacula only to the extent required to gain access to the cleared tibiotalar space. Analogous to the hip joint insertional method, the ankle joint will be prepared arthroscopically under general anesthesia, and may benefit from distal distraction as in total ankle joint replacement surgeries with the DePuy Agility technique pinning above and below the ankle joint and then distracting it. The degree of distraction required in all joints to which this invention is applied, including but not limited to those of all appendicular skeletal structures such as the shoulder, elbow, wrist, phalanges, hip, knee, and ankle, will depend both on the nature anatomy and located pathophysiology that must be accommodated on a case by case basis and said distraction may be a combination of body position using gravitational forces and/or superimposed distracting devices. In the ankle, the surgeon will be developing the interval between the extensor hallucis longus and anterior tibial tendons. Injury tissue is removed, and the implant inserted fitting as preplanned. The implant surface may be provided with roughness, e.g. external mesh, to control movement by friction as described above for the hip joint, and/or attached fixation cords or tabs to connect to proximate ligaments or adjacent boney structures may be used at the surgeon's discretion to balance implant location stability and integrity, with the need for functional joint movements.

Over time, ingrowth of repair tissue aids in fixation and stability externally to the implant, while the soft cushioning implant interior will absorb forces across the joint surfaces and permit proper motion. The tugor or wall tension of the implant as well as the inside distension of the implant per se can be adjusted by adding or removing the inflation substance to the implant's interior space.

Accordingly, the present invention provides a new approach to arthroplasty that involves a resilient implant device deployed between bones of the joint. Whereas a joint is comprised of the interface between bone cartilage space cartilage bone, in certain joint spaces such as the knee, the invention cushion may expand to fit the spaces between both "knee joints"—the femoral tibial involved on standing or walking on a level plane, and the patella femoral bones of the knee more involved on stair ascent and decent. For example, pressures behind the knee cap or patella when lying are zero, when standing are 0.7 times body weight, and when going up and down the patella femoral pressures are 3-4 times body weight. Thus, the implants will need to accommodate all the normal body functional pressures and complex space movements, as described above also in the ankle. When in the hip joint, the normal flexion up to 120 degrees, extension of 20 degrees, abduction of 50 degrees, internal and external rotation of 45 degrees will produce variable axial, shear, and cyclic loads which the implant by design will accommodate and endure as up to 6 times body weight, consistent with a tire on a car that allows for cyclic loads different when driving straight or turning corners. The implant embodying features of the present invention provides more physiologic motion and shock absorption within the joint and has combined characteristics of anatomic design symmetry, balanced rigidity with sufficient attachment connections to adjacent normal structures, and durability that meet the needs of joint reconstruction.

The opposing internal surfaces of the first and second walls of the invention may either move together in synchrony or in opposite directions from one another (e.g. the superior wall moving medially in the hip and the inferior wall moving laterally). Optionally, the implant may be fixed to a concave surface of the joint (e.g., the acetabular hip cup) or to a convex surface of the joint (e.g. the dorsal femoral head surface), to both, or to neither (e.g., having an interference fit within the joint with an expanding balloon or cushion that fills the existing space). The implant may be inserted arthroscopically like a deflated balloon and then inflated through a cannula into the ankle or hip (or other joint structure) to act as a cushion or renewed interface for painless and stable limb motion. When feasible joint capsular and adjacent ligament tissue as well as bone will be left in place to preserve the natural body, unless interfering with reconstructed limb function.

The application of steam in addition to removing damaged debris, can smooth out and reform the joint surface. The high temperature of the steam tends to weld cracks or fissures which can be present in the cartilage surface of a damaged joint. Smoothing of joint surface cartilage with steam welds or seals existing cracks or flaps in the cartilage, especially superficially as the lamina splendors, which melt together to provide a white shiny gliding joint surface. In cases where bone is exposed, the steam can be used to stabilize the periphery of the defect in the joint surface via capsulorrhaphy or joint tightening. Open mechanical and chemical debridement may also be employed to prepare the surfaces for the implant.

Once the implant is secured to the femoral head by means of the skirt or tabs, an impregnated transfer medium or cell template may be used, as described by Histogenics and Tygenix chondrocytes delivery systems wherein the position of concentrated cells is mechanically placed about the implant at areas of greatest cartilage damage to promote regrowth, or as in Carticel wherein watery cells are implanted beneath a periosteal membrane (a wall of the implant serving as the membrane), prior to completion of the inflation or expansion of the implant. At syringe or gauged device with measured screw-home pressure is used to inflate the implant.

Once the joint is ready to receive the implant, the deflated implant is advanced through the diaphragm of a delivery cannula (such as the Acufex from Smith & Nephew) and into the joint. It can be inflated by the attached cannula using a common syringe, inserting several cc's of filler material. Inserted contents and locations of cell placements depend on areas of need and joint size. In the hip implant several cc's of filler material and a viscolubricant in the interior of the implant will allow distension, cushioning, and gliding movements. Cell regeneration agents are placed in the areas of greatest need.

Methods of living stem cell or chondrocyte placement depend on the lesions and specific implant construct. Direct infusion into the joint with completion of implant inflation will press the cells into the hyaline surface, whereupon they attach within the first 24 hours. As a result, the patient should remain sedentary and the joint where the implant is deployed, non-weight bearing for the first day after surgery. Deeper osteochondral defects can be treated by 'hyperperfusion of cells' via either 3-D cell transfer templates, or microneedle injection as used in treatment of diabetic patients for blood sugar testing and insulin/transdermal drug delivery. The cannula attached to the implant may be sealed and detached, or left in place for periodic aspiration of noxious enzymes as for the Cox-1, Cox-2, and 5-Lox systems, followed by reinsertion of activated substances including viscolubricants, or even more cells.

Implants embodying features of the invention may be designed for permanent or temporary deployment within a joint structure. Moreover, the implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. One present method of forming the implant is to apply numerous layers of polymer such as ChronoFlex AR in a solvent and evaporating the solvent after applying each layer.

The skirting or fixation tabs of the present implant prevent joint migration during use. This is in contradistinction with prior solid polymer implants that tended toward dislocation and poor post operative function.

While particular forms of the invention have been illustrated and described herein, it will be apparent that various modifications and improvements can be made to the invention. One alternative implant construction involves the use of an upper portion of the implant having a net-like construction and filled with balls or ball bearing like elements that are larger than the openings in the netting. The balls or ball bearing like elements provide motion to the implant. The netting and ball bearing like elements may include regeneration agents as previously discussed, and the bearing construction may be directed toward favorable implant movement balanced with content disbursement.

The invention is intended primarily for human use but may be extended to mammalian use. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be utilized in another embodiment. Moreover, individual features of one embodiment may be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above are hereby incorporated by reference in their entirety.

What is claimed is:

1. A resilient orthopedic implant comprising:
   a. a first wall configured to engage an articulating end of an acetabulum of a pelvic bone;
   b. a second wall configured to conform around a portion of a femoral head, the second wall having one or more appendages configured to secure the second wall to the femoral head;
   c. a side wall extending between the first wall and the second wall and configured to facilitate relative motion between the first and second walls; and
   d. an interior portion configured to be directly enclosed by the first wall the side wall, and a proximal end of the femoral head;
   wherein some length of the first wall overlaps some length of the second wall creating a fold in the implant such that some length of an exterior surface of the side wall has a concave shape at the fold; and
   wherein the implant is configured for deployment between the femoral head and the acetabulum of the pelvic bone when neither the femoral head nor the pelvic bone is resected.

2. The implant of claim 1 wherein the one or more appendages is a skirt.

3. The implant of claim 1 wherein the one or more appendages are tabs.

4. The implant of claim 1 wherein the one or more appendages are chords.

5. The implant of claim 1 wherein the relative motion between the first and second walls is rotational motion.

6. The implant of claim 1 wherein the relative motion between the first and second walls is linear or curvilinear motion.

7. The implant of claim 1 wherein the relative motion is rotational motion and linear or curvilinear motion.

8. The implant of claim 1 wherein the one or more appendages are configured to be secured to the femur by an adhesive.

9. The implant of claim 1 wherein the first wall has an exterior surface with a convex shape which is configured to contact the acetabulum.

10. The implant of claim 1 wherein the implant comprises a resilient material.

11. The implant of claim 10 wherein the resilient material is a biodurable thermoplastic polyurethane.

12. The implant of claim 10 wherein the resilient material is bioabsorbable.

13. The implant of claim 1 wherein one or more of the walls comprise a plurality of layers.

14. The implant of claim 13 wherein at least one of the layers is porous.

15. The implant of claim 1 wherein the side wall of the implant has reinforcing strands to control expansion upon compression of the implant.

16. The implant of claim 1 wherein the interior portion is configured to be filled with an inflation medium.

17. The implant of claim 16 wherein the inflation medium is a resilient material.

18. The implant of claim 1 wherein a lubricious material is maintained between the first and second walls to facilitate relative motion between the first and second walls.

19. The implant of claim 1, wherein the first wall or the second wall is composed of biocompatible polymeric materials.

20. The implant of claim 1, wherein the first wall, second wall, or side wall comprises numerous layers of one or more polymers.

21. The implant of claim 1, wherein the first wall, second wall, or side wall comprises biocompatible polymeric materials.

22. The implant of claim 1, wherein at least one of the first wall, second wall, or side wall incorporates a lattice.

23. The implant of claim 22, wherein the lattice is configured to hold a therapeutic agent in proximity of an osteochondral defect.

24. The implant of claim 22, wherein the lattice comprises a biocompatible polymer.

25. The implant of claim 1, further comprising a conduit the conduit configured to provide access to the interior portion for injection of a biomaterial into the interior portion while the second wall is fixed to the portion of the femoral head.

* * * * *